United States Patent
Sawhney

(12) 
(10) Patent No.: US 6,673,093 B1
(45) Date of Patent: *Jan. 6, 2004

(54) METHODS AND APPARATUS FOR IN SITU FORMATION OF HYDROGELS

(75) Inventor: Amarpreet S. Sawhney, Bedford, MA (US)

(73) Assignee: Incept LLC, Lexington, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/513,491

(22) Filed: Apr. 21, 2000

Related U.S. Application Data

(62) Division of application No. 09/134,198, filed on Aug. 14, 1998.

(51) Int. Cl.⁷ .................. A61B 17/04; A61M 37/00
(52) U.S. Cl. .................. 606/214; 604/82; 604/240
(58) Field of Search ................. 606/213, 214; 604/82, 197, 240

(56) References Cited

U.S. PATENT DOCUMENTS

| | | | |
|---|---|---|---|
| 3,161,602 A | 12/1964 | Herbig | 252/316 |
| 3,242,237 A | 3/1966 | Belak et al. | 264/13 |
| 3,423,894 A | 1/1969 | Richardson | 52/241 |
| 3,640,741 A | 2/1972 | Etes | 106/170 |
| 3,779,942 A | 12/1973 | Bolles | 252/316 |
| 3,865,108 A | 2/1975 | Hartop | 128/260 |
| 3,991,766 A | 11/1976 | Schmitt et al. | 128/335.5 |
| 3,992,562 A | 11/1976 | Denzinger et al. | 526/208 |
| 4,001,391 A | 1/1977 | Feinstone et al. | 424/45 |
| 4,002,173 A | 1/1977 | Manning et al. | 128/296 |
| 4,014,335 A | 3/1977 | Arnold | 128/260 |
| 4,207,893 A | 6/1980 | Michaels | 128/260 |
| 4,369,229 A | 1/1983 | Shah | 428/421 |

(List continued on next page.)

FOREIGN PATENT DOCUMENTS

| | | | |
|---|---|---|---|
| EP | 0 443 743 | 7/1994 | A23K/1/16 |
| WO | WO 96/39212 | 12/1996 | |

OTHER PUBLICATIONS

Allen, T.M. et al., "Pharmacokinetics of Stealth Versus Conventional Liposomes: Effect of Dose," *Biochimica et Biophysica Acta*, 1068:133–141 (1991).

Allen, T.M. et al., "Liposomes Containing Synthetic Lipid Derivatives of Poly(ethylene glycol) Show Prolonged Circulation Half–Lives In Vivo," *Biochimica et Biophysica Acta*, 1066:29–36 (1991).

Bailey, W.J. et al., "Synthesis of Polymerized Vesicles with Hydrolyzable Linkages," *Macromolecules*, 25:3–11 (1992).

Bhatia, S. et al., "The Effect of Site Implantation and Animal Age on Properties of Polydioxanone Pins," *J. Biomater. Sci., Polymer Edn.*, Bamford, C.H. et al., eds., 6(5):435–446 (1994).

(List continued on next page.)

*Primary Examiner*—Gary Jackson
(74) *Attorney, Agent, or Firm*—Patterson, Thuente, Skaar & Christensen, P.A.

(57) ABSTRACT

Methods and apparatus of forming in situ tissue adherent barriers are provided using a sprayer capable of applying two or more viscous crosslinkable components to tissue. The sprayer comprises separate spray nozzles for each of two or more crosslinkable solutions, with each nozzle surrounded by an annular gas flow outlet. Crosslinkable solutions are stored in separate compartments and communicated under pressure to the spray nozzles. In the presence of gas flow through the annular gas flow outlets, the crosslinkable solutions are atomized and mixed in the gas flow to form a spray. Multi-component hydrogel systems suitable for use with the inventive methods and apparatus are also described.

20 Claims, 2 Drawing Sheets

U.S. PATENT DOCUMENTS

| | | | |
|---|---|---|---|
| 4,530,840 A | 7/1985 | Tice et al. | 514/179 |
| 4,597,970 A | 7/1986 | Sharma et al. | 426/5 |
| 4,631,055 A * | 12/1986 | Redl et al. | 604/82 |
| 4,741,872 A | 5/1988 | DeLuca et al. | 264/4.7 |
| 4,826,945 A | 5/1989 | Cohn et al. | 528/76 |
| 4,828,857 A | 5/1989 | Sharma et al. | 426/285 |
| 4,846,405 A | 7/1989 | Zimmermann | 239/422 |
| 4,938,763 A | 7/1990 | Dunn et al. | 604/891.1 |
| 5,100,992 A | 3/1992 | Cohn et al. | 528/26 |
| 5,160,745 A | 11/1992 | DeLuca et al. | 424/487 |
| 5,171,148 A | 12/1992 | Wasserman et al. | 433/215 |
| 5,198,220 A | 3/1993 | Damani | 424/426 |
| 5,341,993 A | 8/1994 | Haber et al. | 239/331 |
| 5,368,563 A | 11/1994 | Lonneman et al. | 604/82 |
| 5,410,016 A | 4/1995 | Hubbell et al. | 528/354 |
| 5,565,215 A | 10/1996 | Gref et al. | 424/501 |
| 5,582,596 A | 12/1996 | Fukunaga et al. | 604/191 |
| 5,589,194 A | 12/1996 | Tsuei et al. | 424/497 |
| 5,605,541 A | 2/1997 | Holm | 604/82 |
| 5,618,563 A | 4/1997 | Berde et al. | 424/501 |
| 5,650,173 A | 7/1997 | Ramstack et al. | 424/489 |
| 5,693,341 A | 12/1997 | Schroeder et al. | 424/488 |
| 5,740,965 A | 4/1998 | Miyagi et al. | 239/423 |
| 5,759,169 A | 6/1998 | Marx | 604/82 |

OTHER PUBLICATIONS

Dong, L.C. et al., "Dextran Permeation Through Poly (N–Isopropylacrylamide) Hydrogels," *J. Biomater. Sci., Polymer Edn.*, Bamford, C.H. et al., eds., 5(5):473–484 (1994).

Edgington, S.M., "New Horizons for Stem–Cell Bioreactors," *Bio/Technology*, 10:1099–1106 (1992).

*Handbook of Common Polymers*, compiled by Roff, W.J. et al., CRC Press, Cleveland, Ohio.

Jarrett P.K. et al., "Bioabsorbable Hydrogel Tissue Barrier: In Situ Gelation Kinetics," *Soc. for Biomater.*, Transactions of 21st Annual Meeting: 182 (1995).

Klibanov, A.L. et al., "Activity of Amphipathic Poly (ethylene glycol) 5000 to Prolong the Circulation Time of Liposomes Depends on the Liposome Size and Is Unfavorable for Immunoliposome Binding to Target," *Biochimica et Biophysica Acta*, 1062:142–148 (1991).

Lasic, D.D. et al., "Sterically Stabilized Liposomes: A Hypothesis on the Molecular Origin of the Extended Circulation Times," *Biochimica et Biophysica Acta*, 1070:187–192 (1991).

Ley, K. et al., "Endothelial, Not Hemodynamic, Differences Are Responsible for Preferential Leukocyte Rolling in Rat Mesenteric Venules," *Circulation Research*, 69(4):1034–1041 (1991).

Maruyama, K. et al., "Effect of Molecular Weight in Amphipathic Polyethyleneglycol on Prolonging the Circulation Time of Large Unilamellar Liposomes," *Chem. Pharm. Bull.*, 39(6):1620–1622 (1991).

Mayhew, E. et al., "Characterization of Liposomes Prepared by Using a Microemulsifier," *Biochimica et Biophysica Acta*, 775:169–174 (1984).

*Medicinal Chemistry*, 3rd Ed., Parts 1 and 2, Burger, A., ed., Wiley–Interscience.

Nagaoka, S. et al., "Interaction Between Blood Components and Hydrogels with Poly(oxyethylene) Chains," *Polymers As Biomaterials*, Shalaby, S.W. et al. eds., Plenum Press, New York, 361–374 (1984).

Okano, T. et al., "Effect of Hydrophilic and Hydrophobic Microdomains on Mode of Interaction Between Block Polymer and Blood Platelets," *J. Biomed. Mats.. Research*, 15:393–402 (1981).

Onishi, Y. et al., "Study of Dextran–Methyl Methacrylate Graft Copolymer," *Contemporary Topics in Polymer Science*, Bailey, W.J. et al., eds., Plenum Press, New York, 4:149–162 (1984).

Park, K., "Enzyme–Digestible Swelling Hydrogels as Platforms for Long–Term Oral Drug Delivery: Synthesis and Characterization," *Biomaterials*, 9:435–441 (1988).

Park, K. et al., *Biodegradable Hydrogels for Drug Delivery*, Technomic Publishing Co., Inc., Lancaster, PA (1993).

Raud, J. et al., "Leukocyte Rolling and Firm Adhesion in the Microcirculation," *Gastroenterology*, 104:310–314 (1993).

*Remington's Pharmaceutical Sciences*, 14th Ed., J.E. Hoover et al., eds., Mack Publishing Co., Easton, Pennsylvania (1970).

Sawhney, A.S. et al., "Bioerodible Hydrogels Based on Photopolymerized Poly(ethylene glycol)–co–poly($\alpha$–hydroxy acid) Diacrylate Macromers," *Macromolecules*, 26:581–587 (1993).

Shah, K.R., "Novel Two–Phase Polymer System," *Polymer*, 28:1212–1216 (1987).

Shah, K.R., "Hydrophilic–Hydrophobic Domain Polymer Systems," *Water Soluble Polymers*, Chap. 30, Shalaby, S.W. et al., eds. Amer. Chem. Soc., Washington, D.C., 467–483 (1991).

Shalaby, S.W., "Bioabsorbable Polymers," *Encyclopedia of Pharmaceutical Technology*, Swarbrick, J. et al., eds., Marcel Dekker, Inc., New York, 1:465–476 (1988).

Shalaby, S.W. et al., "In Vitro and In Vivo Studies of Enzyme–Digestible Hydrogels for Oral Drug Delivery," *J. Controlled Release*, 19:131–144 (1992).

Silberberg, A., "Network Deformation in Flow," *Molecular Basis of Polymer Networks*, Baumgartner, A. et al., eds., Springer–Verlag, Berlin, 42:147–151 (1989).

Smith, K.L. et al., "Association Reactions for Poly(alkylene Oxides) and Polymeric Poly (carboxylic Acids)," *Ind. Eng. Chem.*, 51(11):1361–1364 (1959).

*The Drug, The Nurse, The Patient (Including Current Drug Handbook)*, Falconer's 7th Ed., W.B. Saunders Co., Philadelphia, Pennsylvania (1974).

Torchilin, V.P. et al., "Liposome–Polymer Systems. Introduction of Liposomes into a Polymer Gel and Preparation of the Polymer Gel Inside a Liposome," *Polymer Sci. U.S.S.R.*, 30(10): 2307–2312 (1988).

Torchilin, V.P. et al., "The Antibody–Linked Chelating Polymers for Nuclear Therapy and Diagnostics," *Critical Reviews in Therapeutic Drug Carrier Systems*, 7(4):275–308 (1991).

Woodle, M.C. et al., "Versatility in Lipid Compositions Showing Prolonged Circulation with Sterically Stabilized Liposomes," *Biochimica et Biophysica Acta*, 1105:193–200 (1992).

* cited by examiner

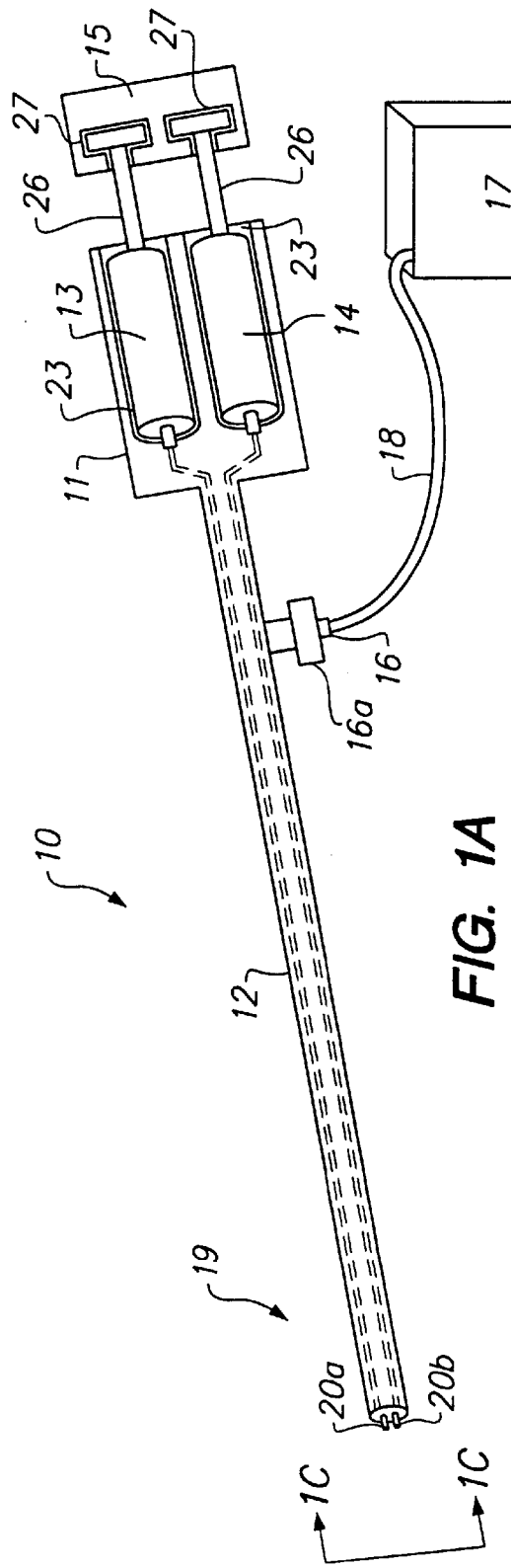
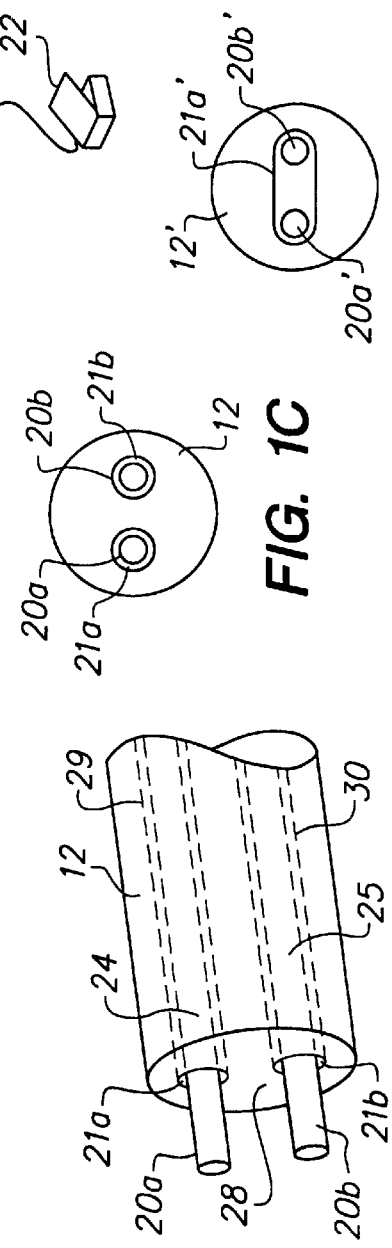
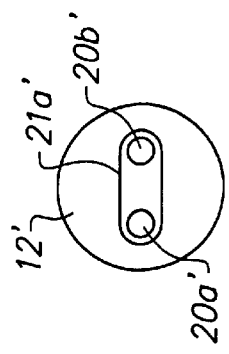
FIG. 1A
FIG. 1B
FIG. 1C
FIG. 1D

METHODS AND APPARATUS FOR IN SITU FORMATION OF HYDROGELS

REFERENCE TO RELATED APPLICATION

This application is a division of U.S. patent application Ser. No. 09/134,198, filed Aug. 14, 1998.

FIELD OF THE INVENTION

This present invention relates generally to methods and apparatus for forming hydrogels in situ, especially during open or minimally invasive surgery. More particularly, the present invention relates to apparatus and methods for delivering two liquid components that form hydrogels upon mixing.

BACKGROUND OF THE INVENTION often during surgery, tissue may be traumatized or compromised such that it needs to be temporarily supported or isolated during the wound healing period. Materials that may be used as tissue sealants also may be used to temporarily support tissue and to seal leaks from tissue until the tissue heals. Tissue sealants that perform these functions are well known in literature and include a variety of natural and synthetic sealants including fibrin sealants, cyanoacrylate based sealants, and other synthetic sealants and polymerizable macromers.

Various types of previously known apparatus have been developed to deliver fibrin sealants, which are derived from blood-based proteins. For example, U.S. Pat. No. 5,605,541 to Holm describes apparatus and methods for applying two or more components of a fibrin sealant. That patent describes a spray head having a central gas discharge port and coaxially arranged annular ports through which respective components of the fibrin sealant are discharged. The spray head may be prone to clogging if the central gas discharge port is restricted.

U.S. Pat. No. 5,368,563 to Lonneman et al. describes a sprayer assembly having angular connecting channels through which components of a fibrin sealant are discharged to cause mixing. U.S. Pat. No. 5,341,993 to Haber et al. describes a hand held sprayer having a remotely actuated spray tip. Both of the devices described in those patents may not be suitable for spraying viscous fluids, which tend to emerge as streams rather than as fine sprays.

U.S. Pat. No. 4,001,391 to Feinstone et al. describes a method for spraying viscous and buttery fluids using a propellant and a pressurized container. The use of propellants is undesirable in medical applications due to uncertain biocompatibility of these materials.

In view of the foregoing, it would be desirable to provide apparatus and methods that enable a tissue coating comprising two or more crosslinkable fluids to be applied in situ as a spray.

It further would be desirable to provide apparatus and methods for spraying polymerizable fluids with reduced risk of clogging of the sprayer.

SUMMARY OF THE INVENTION

In view of the foregoing, it is an object of the present invention to provide apparatus and methods that enable a tissue coating comprising two or more crosslinkable fluids to be applied in situ as a spray.

It is a further object of this invention to provide apparatus and methods for spraying crosslinkable fluids with reduced risk of clogging of the sprayer.

These and other objects of the invention are accomplished by providing a sprayer capable of applying two or more viscous crosslinkable components to tissue to form a coating that adheres to the tissue surface. For example, two crosslinkable solutions, each containing one component of a co-initiating system capable of crosslinking when mixed together, may be placed in separate chambers of the sprayer. When the sprayer is activated, the emergent spray contacts tissue, resulting in mixing and crosslinking of the two solutions to form a coating (for example a hydrogel) on the tissue surface.

In a preferred embodiment, the sprayer comprises separate spray nozzles for each of two or more crosslinkable solutions, with each nozzle surrounded by a separate or common gas flow outlet. The crosslinkable solutions are stored in separate compartments, e.g., a multi-cylinder syringe, and communicated under pressure to the spray nozzles. In the presence of gas flow through the gas flow outlets, the crosslinkable solutions are atomized and mixed in the gas flow to form a spray, which may be used to coat tissue.

The crosslinkable solutions used with the apparatus may be crosslinked using either physical crosslinking, chemical crosslinking, or both. For a chemical initiation process, the two or more crosslinkable solutions may polymerize when mixed in the gas flows during spraying, thus forming an adherent coating that adheres to the tissue surface on contact. If a thermal initiating process is used, the two or more solutions may crosslink after contacting the tissue surface and warming to physiological temperatures.

Alternatively, the two or more solutions may include macromers that contain groups that demonstrate activity towards other functional groups such as amines, imines, thiols, carboxyls, isocyanates, urethanes, amides, thiocyanates, hydroxyls, etc., which may be naturally present in, on, or around tissue or may be optionally provided in the region as part of the instilled formulation required to effect the barrier.

Methods of forming tissue adherent barriers in accordance with the principles of the present invention also are provided.

BRIEF DESCRIPTION OF THE DRAWINGS

Further features of the invention, its nature and various advantages will be more apparent from the accompanying drawings and the following detailed description of the preferred embodiments, in which:

FIGS. 1A, 1B and 1C, are, respectively, a perspective view of a two-fluid sprayer of the present invention, a detailed view of the distal end of the sprayer, and an end view of the distal end of the sprayer taken along line 1C—1C of FIG. 1A;

FIG. 1D is an end view of the distal end of an alternative embodiment of the sprayer of FIG. 1A taken along line 1C—1C;

DETAILED DESCRIPTION OF THE INVENTION

Figure 2A:
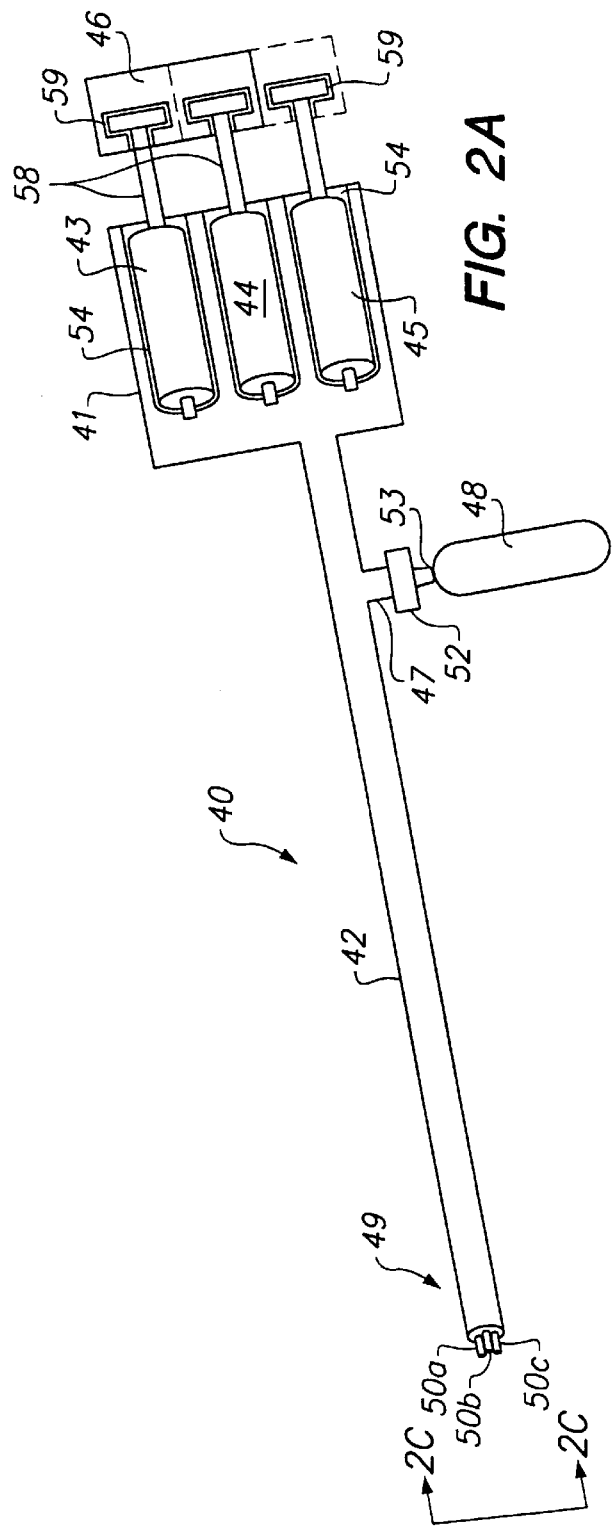
FIGS. 2A, 2B and 2C, are, respectively, a perspective view of an alternative embodiment of the two-fluid sprayer of the present invention, a detailed view of the distal end of the sprayer, and an end view of the distal end of the sprayer taken along line 2C—2C of FIG. 2A.

The present invention is directed to the use of multi-component crosslinkable solutions to form protective coatings on tissue, e.g., to prevent post-surgical adhesions, or as drug delivery layers. In accordance with the methods of the present invention, two or more crosslinkable solutions are sprayed onto tissue during, or near the completion, of surgery to form adherent coatings.

The following written description describes multi-component hydrogel systems suitable for such use, apparatus for dispensing such hydrogel systems, and provides an illustrative example of use of the inventive methods and apparatus.

Hydrogel Systems Suitable For Use

Crosslinkable solutions preferred for use in accordance with the principles of the present invention include those that may be used to form coatings on tissue, and may form physical crosslinks, chemical crosslinks, or both. Physical crosslinks may result from complexation, hydrogen bonding, desolvation, Van der Waals interactions, ionic bonding, etc., and may be initiated by mixing two components that are physically separated until combined in situ, or as a consequence of a prevalent condition in the physiological environment, such as temperature, pH, ionic strength, etc. Chemical crosslinking may be accomplished by any of a number of mechanisms, including free radical polymerization, condensation polymerization, anionic or cationic polymerization, step growth polymerization, etc.

Hydrogels suitable for use in accordance with the principles of the present invention preferably crosslink spontaneously without requiring the use of a separate energy source. Such systems allow good control of the crosslinking process, because gelation does not occur until the sprayer is actuated and mixing of the two solutions takes place. If desired, one or both crosslinkable solutions may contain dyes or other means for visualizing the hydrogel coating. Alternatively, a colored compound may be produced as a byproduct of the reactive process. The crosslinkable solutions also may contain a bioactive drug or therapeutic compound that is entrapped in the resulting coating, so that the coating becomes a drug delivery layer.

Properties of the hydrogen system, other than crosslinkability, preferably should be selected according to the intended application. For example, if the sprayer is to be used to provide a tissue adherent coating in the abdominal cavity to prevent post-surgical tissue adhesion, it is preferable that the hydrogel system have a relatively low tensile strength, to avoid adversely effecting normal physiologic processes of the organs, be near equilibrium hydration when formed, experience relatively little in situ swelling, and be biodegradable.

other applications may require different characteristics of the hydrogel system. There is extensive literature describing the formulation of crosslinkable coating materials for particular medical applications, which formulae may be readily adapted for use herein with little experimentation. More generally, for example, if a hydrogel system is to be used for coating of tissues, cells, medical devices, or capsules, for drug delivery or as mechanical barriers or supports, the materials should be selected on the basis of exhibited biocompatibility and lack of toxicity. For all biologically-related uses, toxicity must be low or absent in the finished state for externally coated non-living materials, and at all stages for internally-applied materials.

Additionally, the hydrogel system solutions should not contain harmful or toxic solvents. Preferably, the solutions are substantially soluble in water to allow application in a physiologically- compatible solution, such as buffered isotonic saline. Water-soluble coatings may form thin films, but more preferably form three-dimensional gels of controlled thickness. It is also preferable in cases that the coating be biodegradable, so that it does not have to be retrieved from the body. Biodegradability, as used herein, refers to the predictable disintegration of the coating into molecules small enough to be metabolized or excreted under normal physiological conditions.

Polymers Suitable for Physical Crosslinking

Physical crosslinking may be intramolecular or intermolecular or in some cases,:both. For example, hydrogels can be formed by the ionic interaction of divalent cationic metal ions (such as $Ca+2$ and $Mg+2$) with ionic polysaccharides such as alginates, xanthan gums, natural gum, agar, agarose, carrageenan, fucoidan, furcellaran, laminaran, hypnea, eucheuma, gum arabic, gum ghatti, gum karaya, gum tragacanth, locust beam gum, arabinogalactan, pectin, and amylopectin. These crosslinks may be easily reversed by exposure to species that chelate the crosslinking metal ions, for example, ethylene diamine tetraacetic acid. Multifunctional cationic polymers, such as poly(1-lysine), poly (allylamine), poly(ethyleneimine), poly(guanidine), poly (vinyl amine), which contain a plurality of amine functionalities along the backbone, may be used to further induce ionic crosslinks.

Hydrophobic interactions are often able to induce physical entanglement, especially in polymers, that induces increases in viscosity, precipitation, or gelation of polymeric solutions. For example, poly(oxyethylene)-poly (oxypropylene) block copolymers, available under the trade name of PLURONIC®, BASF Corporation, Mount Olive, N.J., are well known to exhibit a thermoreversible behavior in solution. Thus, an aqueous solution of 30% PLURONIC® F-127 is a relatively low viscosity liquid at 4° C. and forms a pasty gel at physiological temperatures due to hydrophobic interactions. Other block and graft copolymers of water soluble and insoluble polymers exhibit similar effects, for example, copolymers of poly(oxyethylene) with poly (styrene), poly(caprolactone), poly(butadiene) etc.

Techniques to tailor the transition temperature, i.e. the temperature at which an aqueous solution transitions to a gel due to physical linking, are per se known. For example, the transition temperature may be lowered by increasing the degree of polymerization of the hydrophobic grafted chain or lock relative to the hydrophilic block. Increase in he overall polymeric molecular weight, while keeping the hydrophilic: lipophilic ratio unchanged also leads to a lower gel transition temperature, because the polymeric chains entangle more effectively. Gels likewise may be obtained at lower relative concentrations compared to polymers with lower molecular weights.

Solutions of other synthetic polymers such as poly(N-alkylacrylamides) also form hydrogels that exhibit thermoreversible behavior and exhibit weak physical crosslinks on warming. During spraying of thermoreversible solutions, cooling of the solutions may be expected from evaporation during atomization. Upon contact with tissue target at physiological temperatures, viscosity is expected to increase from the formation of physical crosslinks. Similarly, pH responsive polymers that have a low viscosity at acidic or basic pH may be employed, and exhibit an increase in viscosity upon reaching neutral pH, for example, due to decreased solubility.

For example, polyanionic polymers such as poly(acrylic acid) or poly(methacrylic acid) possess a low viscosity at acidic pHs that increases as the polymers become more solvated at higher pHs. The solubility and gelation of such polymers further may be controlled by interaction with other water soluble polymers that complex with the polyanionic polymers. For example, it is well known that poly(ethylene oxides) of molecular weight over 2,000 dissolve to form clear solutions in water. When these solutions are mixed with similar clear solutions of poly(methacrylic acid) or poly(acrylic acid), however, thickening, gelation, or precipitation occurs depending on the particular pH and conditions used (for example see Smith et al., "Association reactions for poly(alkylene oxides) and poly(carboxylic acids)," *Ind. Eng. Chem*., 51:1361 (1959). Thus, a two component aqueous solution system may be selected so that the first component (among other components) consists of poly (acrylic acid) or poly(methacrylic acid) at an elevated pH of around 8–9and the other component consists of (among other components) a solution of poly(ethylene glycol) at an acidic pH, such that the two solutions on being combined in situ result in an immediate increase in viscosity due to physical crosslinking.

Physical gelation also may be obtained in several naturally existing polymers too. For example gelatin, which is a hydrolyzed form of collagen, one of the most common physiologically occurring polymers, gels by forming physical crosslinks when cooled from an elevated temperature. Other natural polymers, such as glycosaminoglycans, e.g., hyaluronic acid, contain both anionic and cationic functional groups along each polymeric chain. This allows the formation of both intramolecular as well as intermolecular ionic crosslinks, and is responsible for the thixotropic (or shear thinning) nature of hyaluronic acid. The crosslinks are temporarily disrupted during shear, leading to low apparent viscosities and flow, and reform on the removal of shear, thereby causing the gel to reform.

Macromers Suitable for Chemical Crosslinking

Water soluble polymerizable polymeric monomers having a functionality >1(i.e., that form crosslinked networks on polymerization) and that form hydrogels are referred to hereinafter as "macromers". several functional groups may be used to facilitate chemical crosslinking reactions. When these functional groups are self condensible, such as ethylenically unsaturated functional groups, the crosslinker alone is sufficient to result in the formation of a hydrogel, when polymerization is initiated with appropriate agents. Where two solutions are employed, each solution preferably contains one component of a co-initiating system and crosslink on contact. The solutions are stored in separate compartments of a sprayer, and mix either when sprayed or on contact with the tissue.

An example of an initiating system suitable for use in the present invention is the combination of a peroxygen compound in one solution, and a reactive ion, such as a transition metal, in another. Other means for polymerization of macromers to coatings on tissue also may be advantageously used with macromers that contain groups that demonstrate activity towards functional groups such as amines, imines, thiols, carboxyls, isocyanates, urethanes, amides, thiocyanates, hydroxyls, etc., which may be naturally present in, on, or around tissue. Alternatively, such functional groups optionally may be provided in the region as part of the instilled formulation required to effect the barrier. In this case, no external initiators of polymerization are needed and polymerization proceeds spontaneously when two complementary reactive functional groups containing moieties interact at the application site.

Preferred hydrogel systems are those biocompatible multi-component systems that spontaneously crosslink when the components are mixed, but wherein the two or more components are individually stable for the duration of the deposition process. Such systems include, for example,. contain macromers that are di or multifunctional amines in one component and di or multifunctional oxirane containing moieties in the other component. Other initiator systems, such as components of redox type initiators, also may be used. The mixing of the two or more solutions may result in either an addition or condensation polymerization that further leads to the formation of a coating.

Any monomer capable of being crosslinked to form a biocompatible surface coating may be used. The monomers may be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, U.S. Pat. Nos. 4,741,872 and 5,160,745 to De Luca et al., or U.S. Pat. No. 5,410,016 to Hubbell et al.

Preferred monomers are the crosslinkable, biodegradable, water-soluble macromers described in U.S. Pat. No. 5,410,016 to Hubbell et al, which is incorporated herein by reference. These monomers are characterized by having at least two polymerizable groups, separated by at least one degradable region. When polymerized in water, they form coherent gels that persist until eliminated by self-degradation. In the most preferred embodiment, the macromer is formed with a core of a polymer that is water soluble and biocompatible, such as the polyalkylene oxide polyethylene glycol, flanked by hydroxy acids such as lactic acid, having acrylate groups coupled thereto. Preferred monomers, in addition to being biodegradable, biocompatible, and non-toxic, also will be at least somewhat elastic after polymerization or curing.

It has been determined that monomers with longer distances between crosslinks are generally softer, more compliant, and more elastic. Thus, in the polymers of Hubbell, et al., increased length of the water-soluble segment, such as polyethylene glycol, tends to enhance elasticity. Molecular weights in the range of 10,000 to 35,000 of polyethylene glycol are preferred for such applications, although ranges from 3,000 to 100,000 also are useful.

In addition, coatings formed in accordance with the methods of the present invention may be formed as laminates (i.e., having multiple layers). Thus, for example, a lower layer of the laminate may consist of a more tightly crosslinked hydrogel that provides good adherence to the tissue surface and serves as a substrate for an overlying compliant coating to reactively bond thereto. Materials having lower molecular weights between crosslinks may be suitable for use as a base coating layer. Molecular weights in the range of 400 to 20,000 of polyethylene glycol are preferred for such applications, although ranges from 400 to 10,000 are more preferable.

It should be understood, however, that hydrogels that crosslink by a variety of other mechanisms, for example, by interaction of electrophilic and nucleophilic functional groups, also may be advantageously used in accordance[]with the principles of the present invention.

Initiating Systems

Metal ions may be used either as an oxidizer or a reductant in redox initiating systems. For example, in the Example set forth hereinbelow, ferrous ions are used in combination with a peroxide or hydroperoxide to initiate polymerization, or as parts of a polymerization system. In this case, the ferrous ions serve as a reductant. In other previously known initiating systems, metal ions serve as an oxidant.

For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states.

Preferred metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide, etc., may. be used.

Thermal initiating systems may be used rather than the redox-type systems described hereinabove. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Preferred macromers for use in forming tissue coatings using the apparatus of the present invention include any of a variety of in situ crosslinkable macromers that form hydrogel compositions in vivo. These macromers may, for example, be selected from compositions that are biodegradable, crosslinkable, and substantially water soluble macromers comprising at least one water soluble region, at least one degradable region, and statistically more than 1 polymerizable region on average per macromer chain, wherein the polymerizable regions are separated from each other by at least one degradable region. Alternatively, if biodegradability is not desirable, compositions that do not contain the biodegradable segments but are substantially water soluble and crosslink in vivo under acceptable physiological conditions may be used.

Sprayers for Dispensina Hydrogel Coatinas

Referring now to FIGS. 1A, 1B and 1C, an illustrative embodiment of a sprayer constructed in accordance with the principles of the present invention is described. Sprayer 10 comprises body 11 having elongated barrel 12, syringes 13 and 14, actuator 15 and gas inlet port 16 coupled to compressor 17 via flexible hose 18. Distal end 19 of sprayer 10 includes outlet nozzles 20a and 20b surrounded by gas flow outlets 21a and 21b, respectively. Compressor 17 supplies a gas flow, preferably compressed air or carbon dioxide, to sprayer 10 either continuously, or hen activated by footpedal 22. Gas inlet port 16 may include filter 16a to remove particulate contaminants, including bacteria and other microorganisms, from the gas flow.

Body 11 includes compartments 23 into which syringes 13 and 14 are placed so that the outlets of the syringes are coupled in fluid communication with the interior of tubes 24 and 25, respectively. Each of syringes 13 and 14 includes plunger 26 that may be engaged in recesses 27 of actuator 15. Accordingly, when actuator 15 is depressed, an equal volume of crosslinkable solution is dispensed from each of syringes 13 and 14. Alternatively, for some systems it may be desirable to omit actuator 15 and instead spray the crosslinkable solutions onto the tissue in a sequential fashion. In either case, sterile crosslinkable solutions may be stored separately in syringes 13 and 14, and assembled in sprayer 10 as required for a particular application.

Tube 24 extends from the proximal end of barrel 12, where it is coupled to syringe 13, to a point a slightly beyond distal endface 28 of barrel 12, where it forms outlet nozzle 20a. Tube 24 is disposed within lumen 29 that communicates with gas inlet port 16. Gas entering sprayer 10 via gas inlet port 16 flows through the annular space defined by the exterior of tube 24 and the interior surface of lumen 29, exiting sprayer 10 through gas flow outlet 21a. As the gas, preferably air or carbon dioxide, flows through gas flow outlet 21a, it mixes with the crosslinkable solution from syringe 13 passing through outlet nozzle 20a, breaking the crosslinkable solution into fine droplets or a mist.

Likewise, tube 25 extends from the proximal end of barrel 12, where it is coupled to syringe 14, to a point a slightly beyond distal endface 28 of barrel 12, where it forms outlet nozzle 20b. Tube 25 is disposed within lumen 30 that communicates with gas inlet port 16. Thus, gas entering sprayer 10 via gas inlet port 16 flows through the annular space defined by the exterior of tube 25 and the interior surface of lumen 30, exiting sprayer 10 through gas flow outlet 21b. As the gas flows through gas flow outlet 21b, it mixes with the crosslinkable solution from syringe 14 passing through outlet nozzle 20b, also breaking the crosslinkable solution into fine droplets or a mist.

Outlet nozzles 20a and 20b are preferably arranged so that the crosslinkable droplets or mist formed by outlet nozzle 20a and gas flow outlet 21a converges with that formed by outlet nozzle 20b and gas flow outlet 21b to provide a spray containing a mixture of the two crosslinkable solutions. As described hereinabove, the two solutions may either crosslink on contact within the spray, or crosslink upon contacting the tissue. Outlet nozzles 20a and 20b preferably extend several millimeters beyond distal endface 28 of barrel 12 to prevent clogging of the nozzles by premature crosslinking of the emergent fluids by cross-contamination.

Alternatively, outlet nozzles 20a and 20b and gas flow outlets 21a and 21b may be configured so that the movement of the gas flows from gas flow outlets 21a and 21b cause the crosslinkable solutions to be drawn out of nozzles 20a and 20b and entrained in the gas flows by a Venturi effect. In this case, no manual actuation or compression of the crosslinkable solutions is required, and plungers 26 and actuator 15 may be omitted. As a further alternative, instead of using footpedal 22 to regulate the gas flow, compressor 17 may be regulated with a valve (not shown) disposed on body 11 or barrel 12, that selectively diverts gas flow from lumens 29 and 30. This feature may be particularly useful when the sprayer is used in closed relatively fluid tight cavities, such as the pneumoperitoneum created during laparoscopic or pelvic surgery.

Body 11, barrel 12 and actuator 15 preferably are constructed from a plastic such a polyethylene, while tubes 24 and 25 preferably comprise a rigid material, such as stainless steel. Syringes 13 and 14 may comprise materials typically used in medical devices, while compressor 17 and flexible hose 18 may be of the type commercially available, for example, that are used with airbrushes.

In operation, sprayer 10 is coupled to compressor 17 via flexible hose 18. Syringes 13 and 14 are inserted into compartments 23 of body 11 and plungers 26 of syringes 13 and 14 are engaged in recesses 27 in actuator 15. Distal end 19 of sprayer 10 is disposed within a body cavity, for example, intraoperatively in the abdomen or laparoscopically in the pneumoperitoneum, a few inches from tissue to be coated. Footpedal 22 is then depressed to activate compressor 17, while actuator 15 is depressed to dispense crosslinkable solutions from outlet nozzles 20a and 20b. As the solutions emerge from nozzles 20a and 20b, they are atomized and mixed, and directed onto the tissue to be coated. As a result of crosslinking, for example, induced by free radical or chemical crosslinking, the solutions form a film that adheres to the tissue to provide a therapeutic benefit.

In FIG. 1D, an alternative embodiment is depicted in which barrel 12' includes outlet nozzles 20a' and 20b' disposed within single gas flow outlet 21a' and gas flow lumen 29'. Operation of this alternative embodiment is similar to that described hereinabove, except that the crosslinkable solutions are entrained from outlet nozzles 20a' and 20b' by a single stream of gas exiting gas flow outlet 21a'. In addition, the sprayer may include a valve or valves (not shown) for regulating the amount of crosslinkable solution and gas existing outlet nozzles 20a', 20b' and 21a', respectively. Such valves also may permit a jet of gas to be directed onto a targeted tissue, for example, to displace saline or body fluids to dry or clean the target tissue prior to instillation of the hydrogel barrier.

Figure 2C:
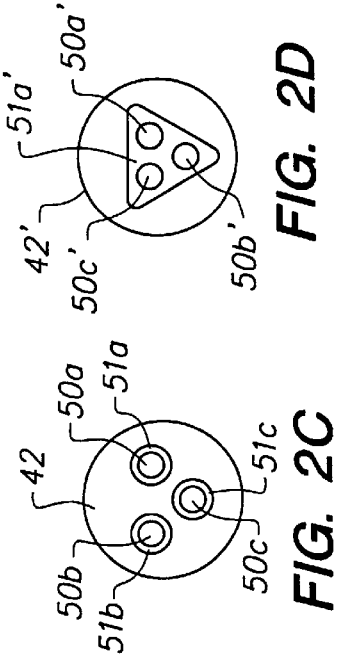
Figure 2D:
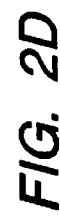
FIG. 2D is an end view of the distal end of an alternative embodiment of the sprayer of FIG. 2A taken along line 2C—2C.
Figure 2B:
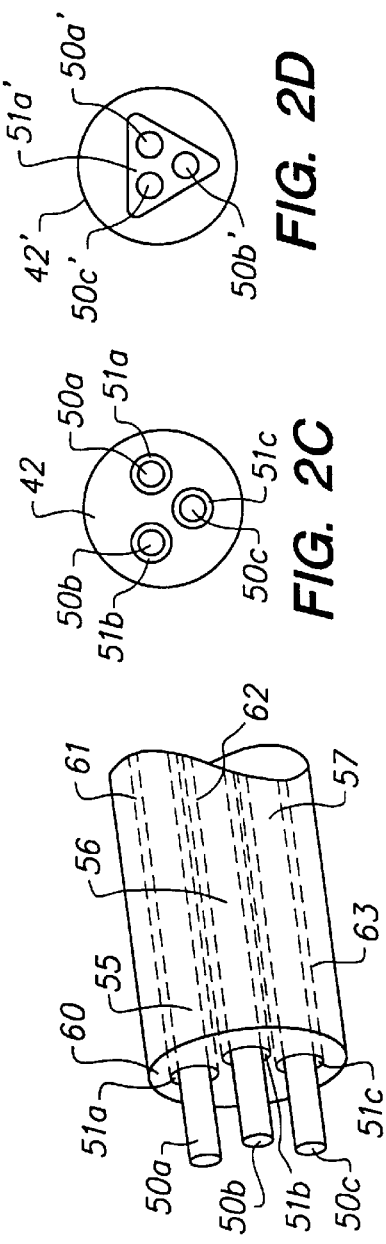

Referring now to FIGS. 2A, 2B and 2C, an alternative embodiment of a sprayer of the present invention for forming adherent tissue coatings from a three-part hydrogel system is described. Sprayer 40 comprises body 41 having elongated barrel 42, syringes 43, 44 and 45, actuator 46 and gas inlet port 47 coupled compressed gas cylinder 48. Distal end 49 of sprayer 40 includes outlet nozzles 50a, 50b and 50c surrounded by gas flow outlets 51a, 51b and 51c, respectively. Compressed gas cylinder 48 is coupled to gas inlet port 47 via valve 52 and filter 53. Valve 52 is configured, for example, so that it may be selectively opened or closed by rotating the valve a half-turn. Filter 53 serves the same functions as filter 16a in the embodiment of FIGS. 1.

Body 41 includes compartments 54 into which syringes 43, 44 and 45 are placed so that the outlets of the syringes are coupled in fluid communication with tubes 55, 56 and 57, respectively. Each of syringes 43–45 includes plunger 58 that may be engaged in recesses 59 of actuator 46. Actuator 46 may link all three of plungers 58 together for common motion, or may be used to link only two of the plungers together, as illustrated by the dotted line in FIG. 2A. Actuator 46 may therefore be depressed to dispense equal volumes of crosslinkable solution from each of syringes 43–45 or just a subset thereof. As in the embodiment of FIG. 1A, the construction of sprayer 40 permits the sterile crosslinkable solutions to be stored separately in syringes 43–45, and assembled in sprayer 40 as required for a particular application.

Tube 55 extends from the proximal end of barrel 42, where it is coupled to syringe 43, to a point a slightly beyond distal endface 60 of barrel 42, where it forms outlet nozzle 50a. Tube 55 is disposed within lumen 61 that communicates with gas inlet port 47. Gas entering sprayer 40 via gas inlet port 47 flows through the annular space defined by the exterior of tube 55 and the interior surface of lumen 61, exiting sprayer 40 through gas flow outlet 51a. As the gas, preferably air or carbon dioxide, flows through gas flow outlet 51a, it mixes with the crosslinkable solution from syringe 43 passing through outlet nozzle 50a, and atomizes the crosslinkable solution into fine droplets or a mist. Tube 56, disposed in lumen 62, and tube 57, disposed in lumen 63, are similarly arranged to atomize crosslinkable solutions from syringes 44 and 45 in the gas flows exiting gas flow outlets 51b and 51c.

Outlet nozzles 50a–50c are preferably arranged so that the atomized crosslinkable solutions converge to provide a spray containing a mixture of the crosslinkable solutions. As in the previous embodiment, outlet nozzles 50a–50c preferably extend several millimeters beyond distal endface 60 of barrel 42 to prevent clogging of the nozzles by premature crosslinking of the emergent fluids by crosscontamination. Alternatively, outlet nozzles 50a–50c and gas flow outlets 51a–51cmay be configured so that the gas exiting gas flow outlets 51a–51c cause the crosslinkable solutions to be drawn out of the nozzles by a Venturi effect, as described hereinabove.

With respect to FIG. 2D, an alternative embodiment is depicted in which barrel 42' includes outlet nozzles 50a', 50b' and 50c' disposed within single gas flow outlet 51a' and gas flow lumen 61'. Operation of this alternative embodiment is similar to that described hereinabove, except that the crosslinkable solutions are entrained from outlet nozzles 50a', 50a' and 50c' by a single stream of gas exiting gas flow outlet 51a'. In addition, like the embodiment described with respect to FIG. 1D, the sprayer may include a valve or valves for regulating the amount of crosslinkable solution and gas existing the outlet nozzles, and also may permit a jet of gas to be directed onto a targeted tissue to displace saline or body fluids, thereby drying or cleaning the target tissue prior to instillation of the hydrogel barrier.

The embodiments of FIG. 2 may be advantageously used to dispense a three component hydrogel system to form an adherent therapeutic layer on a tissue surface. Alternatively, syringes 43 and 44 may contain components of crosslinkable solution that are activated to initiate crosslinking by mixing the two solutions. Syringe 45 may then contain a further crosslinkable solution that enhances adherence of the coating to tissue, for example, by providing a highly crosslinked network as the base coat or by helping the top coat adhere better to the tissue surface by other mechanisms.

The advantages and benefits of the methods and apparatus of the invention are clearly demonstrated by the following example, which is provided for purposes of illustration, and not limitation of the invention. Other such uses will be apparent to those familiar with the art.

EXAMPLE

Sprayer 10 of FIG. 1 is used in conjunction with aqueous solutions of crosslinkable monomers. Solution 1, consisting of a 10% solution of a polyethylene glycol diacrylate (M.W. 3,000 Da, purchased from Shearwater Polymers, Huntsville, Ala.) dissolved in normal saline (pH 5–6) and containing 500 ppm of hydrogen peroxide is drawn up in syringe 13, preferably a 5 cc syringe. Solution 2, consisting of a 10% solution of a polyethylene glycol diacrylate dissolved in normal saline (pH 5–6) and containing 5000 ppm of ferrous sulfate peroxide, is drawn up in syringe 14, also a 5 cc syringe. Syringes 13 and 14 are individually loaded in compartments 23, and are coupled to tubes 24 and 25 and actuator 15.

Airflow from a regulated source of compressed air (an air compressor such as those commercially available for airbrushes) is connected to the sprayer 10 using a piece of tubing. When actuator 15 is depressed, a steady spray of the two liquid components will be observed. When this spray is directed to a piece of tissue a hydrogel coating will be observed to form on the surface of the tissue. The hydrogel coating is resistant to rinsing and is well adhered to the tissue surface. Within a short period of time (less than a minute) an area of 10 cm×5 cm may be coated with ease.

While preferred illustrative embodiments of the invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. A method of forming an adherent coating on a tissue surface comprising: providing a sprayer having a first chamber containing a first component, a second chamber containing a second component, a first nozzle coupled to the first chamber, and a second nozzle coupled to the second chamber, a gas flow outlet surrounding the first and the second nozzles, and a source of pressurized gas coupled to the gas flow outlet;

spraying the first component from the first chamber through the first nozzle onto the tissue surface; and spraying the second component from the second chamber through the second nozzle onto the tissue surface; thereby reacting the first component with the second component to form coating on the tissue surface.

2. The method of claim 1 wherein spraying the first component from the first chamber onto the tissue surface and spraying the second component from the second chamber onto the tissue surface further comprises simultaneously spraying the first component from the first chamber and the second component from the second chamber onto the tissue surface.

3. The method of claim 1 further comprising warming the first and the second components to physiological temperatures.

4. The method of claim 1 wherein crosslinking the first and second components comprises crosslinking the first and second components by a physical crosslinking process.

5. The method of claim 1 comprising adding an addition-polymerizable or condensation-polymerizable compound to the first chamber.

6. The method of claim 1 wherein the first component is an electrophilic compound and the second component is a nueleophilic compound such that the mixing of the first and second components causes the formation of a hydrogel that coats the tissue.

7. The method of claim 1 wherein the coating is deposited to form a barrier that reduces leakage of body fluids.

8. The method of claim 1 wherein the coating is deposited to form a barrier that reduces formation of post-surgical adhesions.

9. The method of claim 1 wherein the coating contains biologically-active therapeutic materials for release to the tissue.

10. The method of claim 1 further comprising displacing fluid from the tissue surface prior to spraying the first and second components.

11. The method of claim 1 further comprising forming the coating on the tissue surface with biologically-active therapeutic materials mixed therein.

12. The method of claim 1 wherein the first chamber is separable from the sprayer.

13. The method of claim 6 wherein the first component further comprises a second electrophilic compound.

14. A method of forming a coating on a tissue surface comprising:

providing a sprayer having a first chamber containing a first component, a second chamber containing a second component, a first nozzle coupled to the first chamber, a second nozzle coupled to the second chamber, a gas flow outlet.-disposed surrounding the first and the second nozzles, and a source of pressurized gas coupled to the gas flow outlet;

causing the first component to flow from the first nozzle;

causing the second component to flow from the second nozzle; and atomizing at least the first component;

thereby reacting the first component with the second component to form a coating on the tissue surface.

15. The method of claim 14 wherein the first chamber is detachably coupled to the first nozzle.

16. The method of claim 14 wherein the gas flow outlet is selectively coupled to the source of pressurized gas.

17. The method of claim 14 further comprising using at least one plunger to displace at least one of the components.

18. The method of claim 14 further comprising disposing the first component in a first solution and a second component in a second solution, and causing the first solution to flow from the first nozzle and the second solution to flow from the second nozzle by configuring the first and second nozzles and the gas flow outlet to induce a venturi effect to draw the first and second solutions from the first and second nozzles, respectively.

19. The method of claim 18 further comprising atomizing the second solution.

20. The method of claim 14 further comprising forming the coating on the tissue surface with biologically-active therapeutic materials mixed therein.

* * * * *